United States Patent [19]

Kovacs

[11] 4,137,757
[45] Feb. 6, 1979

[54] COMPRESSION TESTING APPARATUS
[75] Inventor: Austin Kovacs, Enfield, N.H.
[73] Assignee: The United States of America as represented by the Secretary of the Army, Washington, D.C.
[21] Appl. No.: 874,442
[22] Filed: Feb. 2, 1978
[51] Int. Cl.² ............................................. G01N 3/08
[52] U.S. Cl. ..................................... 73/860; 100/295; 73/818
[58] Field of Search ...................... 73/94, 93; 100/295

[56] References Cited
U.S. PATENT DOCUMENTS

| | | | |
|---|---|---|---|
| 2,972,249 | 2/1961 | McRae et al. | 73/94 x |
| 3,975,950 | 8/1976 | Erdei | 73/94 |

Primary Examiner—Jerry W. Myracle
Attorney, Agent, or Firm—Thomas O. Maser

[57] ABSTRACT

A testing apparatus comprising two platens one of which is a self-aligning specimen contacting platen which includes an upper portion comprising a first member which contacts the specimen and a second member which is spaced from a base by a plurality of balls. The first and second members are movable relative to each other to pivot the specimen into proper alignment between the platens when the specimen is subjected to compression. The plurality of balls are juxtaposed between and engage the second member of the upper portion and the base and serve to support the upper portion for lateral and rotational movement relative to the base to facilitate alignment.

10 Claims, 1 Drawing Figure

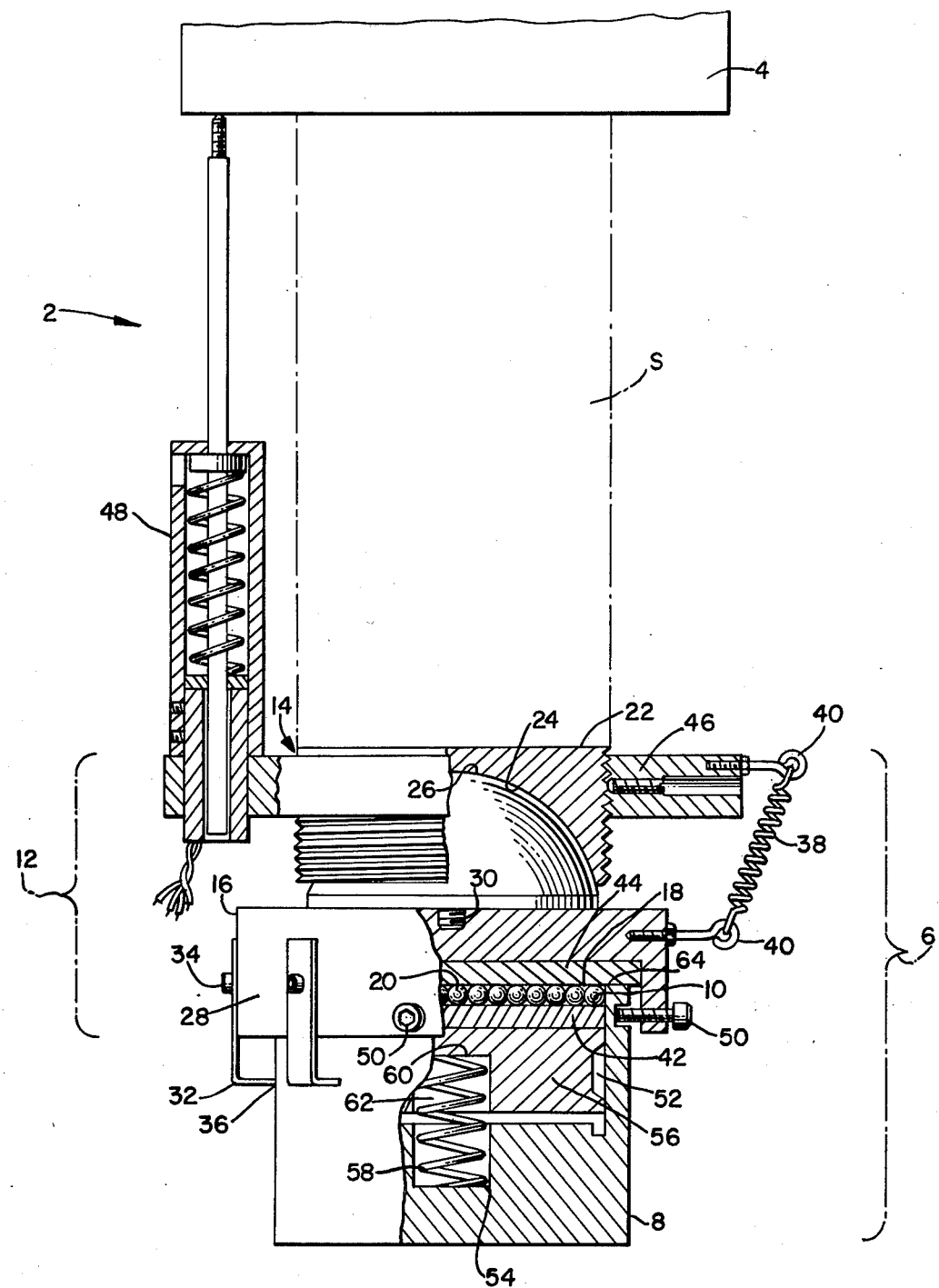

COMPRESSION TESTING APPARATUS

The invention described herein may be manufactured, used, and licensed by or for the Government for Governmental purposes without the payment to me of any royalties thereon.

BACKGROUND OF THE INVENTION

The invention is directed to test equipment for measuring physical characteristics of a specimen. More particularly, the invention relates to compression testing apparatus for measuring specimen deflection and identifying specimen failure when a specimen is subjected to a load. In practice, the pressure applied to the specimen is ordinarily measured while the specimen is being stressed to failure. The accuracy of such measurements depends upon proper alignment of the specimen and the test equipment to assure that the pressure applied to the specimen is uniformly distributed over the area subjected to the compression. To obtain uniform pressure distribution it is necessary to position the specimen in the test equipment in such a manner that the bearing surfaces or platens which engage the specimen therebetween are parallel with the respective surfaces of the specimen with which such platens come into contact. If adjacent surfaces are not properly matched, the portion of the specimen at the point of initial contact by the platen will be subjected to the compressive forces of the test equipment when loading commences, and overloading of the specimen at that point will occur and cause specimen failure at a stress level lower than would have been obtained if the specimen was uniformly loaded. This invention provides improved means to prevent such non-axial loading.

Prior attempts to assure the uniform distribution of pressure applied to a specimen have included the use of what might be referred to as ball-joint engagement of at least one of the load bearing platens of the test equipment. In such equipment at least one of the platens comprises a hemispherical member seated in a convex cavity in a support. In operation, as opposing platens engage opposite ends of the specimen, the hemispherical member moves within the convex cavity in a manner similar to the movement effected between the parts which form a ball-joint structure. It is believed that alignment between the platens and specimen is obtained as a result of the movement or pivoting of the hemispherical member (ball) within the convex cavity (socket) until such time as the load bearing surface associated with the hemispherical member uniformly engages the end of the specimen. One disadvantage of such a mechanism occurs in those instances where equipment is used which requires the manipulation of the specimen by the individual performing the test to obtain proper alignment. In such instances, obtaining alignment is a sensing procedure involving movement of the specimen by hand as the specimen contacting ball-type platen pivots about the socket-type support. The use of such an apparatus may or may not result in perfect seating. Further alignment is not possible after loading commences since to further align the specimen would require lateral translation of one of the platens. Prior art testing equipment does not include this latter feature.

Other prior art test equipment utilizes complex mechanisms. For example, in some equipment alignment between the test specimen and load bearing platens is obtained by subjecting flexible diaphragms to fluid under pressure. Such diaphragms act upon pressure plates which transmit pressure to the specimen to conform to the ends thereof.

Accordingly, it is an object of this invention to provide a testing apparatus which compresses a specimen so that the pressure is uniformly distributed over the area subjected to the compression.

Another object of this invention is to provide a testing apparatus having a specimen contacting platen which may be translated laterally.

Still another object of this invention is to provide a testing apparatus having a specimen contacting platen which may be rotated 360°.

A further object of this invention is to provide a testing apparatus which includes a specimen contacting platen having a ball-joint engagement and which also may be subjected to lateral translation and rotated 360°.

Still a further object of this invention is to provide a testing apparatus which may be manipulated by the individual performing the test, after loading commences, to automatically align the specimen.

Yet another object of this invention is to provide a testing apparatus which does not comprise a complex mechanism.

SUMMARY OF THE INVENTION

This invention achieves these and other objects by providing a testing apparatus which comprises an upper platen and a self-aligning lower platen spaced therefrom. At least one of the platens is movable relative to the other for testing a specimen positioned between the two. The lower platen comprises (a) a base having an upper bearing surface and (b) an upper portion, including a first member for contacting the specimen and a second member mating with the first member and having a lower bearing surface. The first and second members are movable relative to each other for pivoting the specimen into alignment between the platens. The lower platen also comprises a plurality of balls juxtaposed between and in engagement with the upper and lower bearing surfaces. The balls serve to support the upper portion for lateral and rotational movement relative to the base to facilitate alignment of the specimen.

DESCRIPTION OF DRAWINGS

This invention may be clearly understood by reference to the attached drawing which is a partial sectional view of the preferred embodiment of the testing apparatus.

DESCRIPTION OF PREFERRED EMBODIMENT

The embodiment of this invention which is depicted in the drawing is one which is particularly suited for achieving the objects of this invention. The drawing depicts the testing apparatus 2 of this invention. Testing apparatus 2 comprises an upper ridgidly fixed platen 4 and a lower platen 6 spaced therefrom. Lower platen 6 is movable relative to upper platen 4 at least to the extent that after the specimen S has been positioned upon the platen 6, the platen 6 may be moved vertically to engage platen 4 for testing the specimen positioned therebetween. The mechanism utilized to move one platen relative to the other can be any of many well known structures used for the purpose of compressing a specimen between platens until the specimen has been stressed to failure. For example, the structure may be of the type which allows the platens to be moved hydraulically such as is referred to in the patent to Templin, U.S.

Pat. No. 2,346,281. It will, of course, be understood that various other structures may be utilized to effect relative movement of the platens. Other structures include, without limitation, manual, mechanical and pneumatic means for obtaining such movement.

Lower platen 6 comprises (a) a base 8 having an upper bearing surface 10 and (b) an upper portion 12 including a first member 14 for contacting the specimen and a second member 16 mating with the first member 14. Second member 16 includes a lower bearing surface 18. The first member 14 and the second member 16 are movable relative to each other for pivoting the specimen into alignment between upper platen 4 and lower platen 6. A plurality of balls 20 are juxtaposed between and in engagement with upper bearing surface 10 and lower bearing surface 18 to support upper portion 12 for lateral and rotational movement relative to base 8 to facilitate alignment of the specimen. By use of the term "balls" is meant what is usually referred to as balls or ball bearings as well as any other means (e.g. an air bearing or electromagnetic leviation) which may be juxtaposed between and engage the upper bearing surface 10 and lower bearing surface 18 and allow the specimen S to be self aligned as a result of the free lateral and rotational movement of the upper portion 12 relative to the base 8.

In the embodiment depicted in the drawing first member 14 comprises one surface 22 for contacting the specimen S and an opposing concave surface 24. The second member 16 comprises a hemispherical surface 26 which is opposite said lower bearing surface 18. In this embodiment, the mating of the second member 16 with the first member 14 comprises the seating of the hemispherical surface 26 with the concave surface 24 in a ball-joint arrangement such that concave surface 24 may be moved or pivoted upon hemispherical surface 26 in a manner similar to which a socket pivots about a ball.

As depicted in the drawing, the second member 16 comprises a cap 28, one surface of which includes lower bearing surface 18 and the opposite surface of which comprises the hemispherical surface 26. In practice, hemispherical surface 26 may be integral with cap 28, or may be attached thereto as by bolt 30.

Preferably, means for centering the cap 28 relative to the base 8 are connected to the cap and engage the base. For example, leaf springs 32 are connected to cap 28 by means of bolts 34 and engage base 8 at position 36.

Similarly, preferably means for maintaining the specimen contact surface 22 level when lower member 16 is moved relative to upper platen 4 for testing the specimen are connected to the first member 14 and the cap 28. For example, tension springs 38 (only one shown for illustration) are connected to first member 14 and cap 28 by means of bolts 40.

The degree of accuracy of the testing apparatus 2 can be furthered by controlling the degree of hardness and flatness of the upper bearing surface 10 and the lower bearing surface 18, each of which contact the balls 20. For example, upper bearing surface 10 may comprise a precision insert 42. Similarly, lower bearing surface 18 may comprise a precision insert 44. An example of such a precision insert is a highly polished and hardened steel material. Such an insert can be produced having a flatness better than 1/100,000ths of an inch.

As depicted in the drawing first member 14 comprises a collar 46 connected thereto. In this embodiment tension spring 38 is affixed to first member 14 by means of collar 46. Also connected to collar 46 and upper platen 4 is means for measuring any deflection of the specimen S during testing thereof. For example, collar 46 may support a plurality of linear variable differential transformer assemblies 48 (only one shown for illustration) which are of the type which allow measurement of the deflection of specimen S, when it is under load, without sensing compliance strains within the apparatus 2 as various components are loaded and give elasticity. Such transformers are well known in the art.

In operation, specimen S is placed upon specimen contacting surface 22 and lower platen 6 is lifted upward toward the upper platen 4. Upon contact with platen 4 the specimen S is automatically seated in such a manner that the surfaces of the platens 4, 6 are parallel with the respective specimen surfaces which each platen engages. Such automatic seating is effected as a result of the free lateral and rotational movement of cap 28 upon balls 20, which movement allows the specimen contacting surface 22 to pivot the specimen into proper seating alignment between the upper and lower platens as the concave surface 24 pivots upon the hemispherical surface 26.

In those instances when lateral translation of upper portion 12 relative to base 8 is not desired during testing of the specimen (i.e. after initial specimen alignment), means for preventing movement of the upper portion relative to the base may be provided. For example, cap 28 has been provided with locking screws 50 which may be seated against the side of base 8 to prevent lateral movement thereof. Alternatively, base 8 may be provided with a cavity 52 having a bottom well 54. In this embodiment upper bearing surface 10 comprises a movable support member 56. Also provided within cavity 52 are resilient means for urging the support member 56 towards balls 20 which are thereby urged against lower bearing surface 18. For example, spring 58 may be provided between the bottom of well 54 of cavity 52 and the top of well 60 of cavity 62 of support member 56. In this embodiment initial loading allows for the alignment of specimen S as described above and causes downward deflection of cap 28 as support member 56 compresses spring 58. Additional loading of the specimen causes further compression of spring 58 until any further downward deflection of cap 28 is prevented as a result of its engaging base 8 at position 64. The friction incurred at the cap-base interface 64 as loading of the specimen is increased in effect locks the cap and base together to prevent lateral displacement of the cap. Although the use of spring 58 has been described, other resilient means include without limitation pnuematic means such as air under pressure, and hydraulic or electromagnetic means.

The embodiments which have been described herein are but some of several which utilize this invention and are set forth here by way of illustration but not of limitation. It is apparent that many other embodiments which will be readily apparent to those skilled in the art may be made without departing materially from the spirit and scope of this invention.

What is claimed is:

1. Testing apparatus comprising an upper platen and a lower platen spaced therefrom, at least one of said platens being movable relative to the other for testing a specimen positioned therebetween, said lower platen comprising (a) a base having an upper bearing surface;

(b) an upper portion including a first member for contacting said specimen and a second member mating with said first member and having a lower bearing surface, said first and second members being movable relative to each other for pivoting said specimen into alignment between said platens; and (c) a plurality of balls juxtaposed between and in engagement with said surfaces and serving to support said upper portion for lateral and rotational movement relative to said base to facilitate said alignment.

2. The apparatus of claim 1 wherein said first member comprises one surface for contacting said specimen and an opposing concave surface, said second member comprises a hemispherical surface which is opposite said lower bearing surface, and said mating comprises the seating of said hemispherical surface with said concave surface.

3. The apparatus of claim 2 wherein said second member further comprises a cap, one surface of which comprises said lower bearing surface and the opposite surface of which comprises said hemispherical surface.

4. The apparatus of claim 3 wherein means for centering said cap relative to said base are connected to said cap and engage said base.

5. Testing apparatus comprising an upper platen and a lower platen spaced therefrom, at least one of said platens being movable relative to the other for testing a specimen positioned therebetween, said lower platen comprising:

(a) a base having an upper bearing surface;

(b) an upper portion comprising a first member for contacting said specimen, said first member comprising one surface for contacting said specimen and an opposing concave surface, and a second member mating with said first member and having a lower bearing surface, said second member comprising a hemispherical surface which is opposite said lower bearing surface, said mating comprising the seating of said hemispherical surface with said concave surface, said first and second members being movable relative to each other for pivoting said specimen into alignment between said platens, said second member further comprising a cap, one surface of which comprises said lower bearing surface and the opposite surface of which comprises said hemispherical surface, wherein means for centering said cap relative to said base are connected to said cap and engage said base;

(c) a plurality of balls juxtaposed between and in engagement with said surfaces and serving to support said upper portion for lateral and rotational movement relative to said base to facilitate said alignment; and (d) means connected to said first member and said cap for maintaining said specimen contacting surface level when said one platen is moved relative to said other platen for testing said specimen.

6. The apparatus of claim 5 wherein said upper and lower bearing surfaces comprise precision inserts.

7. The apparatus of claim 6 wherein said first member includes a collar connected thereto, said levelling means are connected to said collar and said cap, and means for measuring any deflection of said specimen during said testing are connected to said collar and said upper platen.

8. The apparatus of claim 7 wherein said cap includes means for preventing movement of said upper portion relative to said base connected to said cap.

9. The apparatus of claim 5 wherein said base includes a cavity having a bottom well, said upper bearing surface comprises a movable support member positioned within said cavity, and resilient means, for urging said support member towards said balls which are thereby urged against said lower bearing surface, are contained within said cavity.

10. The apparatus of claim 9 wherein said resilient means is a spring positioned between said support member and said bottom wall.

* * * * *